(12) United States Patent
Lombardi (10) Patent No.: US 9,498,108 B1
(45) Date of Patent: Nov. 22, 2016

(54) DISPOSABLE SHEATH DEVICE

(71) Applicant: Edward J Lombardi, Derry, NH (US)

(72) Inventor: Edward J Lombardi, Derry, NH (US)

(73) Assignee: OPPORTUNITY/DISCOVERY LLC, Wilmington, MA (US)

( * ) Notice: Subject to any disclaimer, the term of this patent is extended or adjusted under 35 U.S.C. 154(b) by 0 days.

(21) Appl. No.: 14/697,825

(22) Filed: Apr. 28, 2015

(51) Int. Cl.
*A61B 1/00* (2006.01)
*A61B 1/04* (2006.01)
*A61M 31/00* (2006.01)
*A61M 37/00* (2006.01)
*A61B 1/307* (2006.01)

(52) U.S. Cl.
CPC ....... *A61B 1/00142* (2013.01); *A61B 1/00128* (2013.01); *A61B 1/307* (2013.01)

(58) Field of Classification Search
USPC ........ 600/104, 106, 107, 114–115, 121–125, 600/127, 129, 153, 154, 156–159, 175; 606/1, 205–209; 604/93.01, 94.01, 604/524, 35
See application file for complete search history.

(56) References Cited

U.S. PATENT DOCUMENTS

| | | |
|---|---|---|
| 3,794,091 A | 2/1974 | Ersek et al. |
| 3,809,072 A | 5/1974 | Ersek et al. |
| 4,646,722 A | 3/1987 | Silverstein et al. |
| 4,741,326 A | 5/1988 | Sidall et al. |
| 4,907,395 A | 3/1990 | Opie et al. |
| 4,991,564 A | 2/1991 | Takahashi et al. |
| 4,991,565 A | 2/1991 | Tkahashi et al. |
| 5,025,778 A * | 6/1991 | Silverstein ........... A61B 1/0008 600/104 |
| 5,237,984 A | 8/1993 | Williams, III et al. |
| 5,386,817 A | 2/1995 | Jones |
| 5,419,310 A | 5/1995 | Frassica et al. |
| 5,556,367 A * | 9/1996 | Yabe .................. A61B 1/00096 600/121 |
| 5,702,348 A | 12/1997 | Harhen |
| 5,910,104 A | 6/1999 | Dobak, III et al. |
| 6,110,103 A | 8/2000 | Donofrio |
| 6,126,592 A | 10/2000 | Proch et al. |
| 6,171,235 B1 | 1/2001 | Konstorum et al. |

(Continued)

*Primary Examiner* — Ryan Henderson (57) ABSTRACT

A disposable sheath device for use with an endoscope is disclosed. The endoscope has a body with an insertion tube having optics at its distal end. The disposable sheath device has a primary lumen and at least one secondary lumen attached to the primary lumen along a length of the lumen. The primary lumen is for covering and protecting the insertion tube from bodily contamination. The secondary lumen is for accommodating a desired tool. The secondary lumen has an insert substantially commensurate in length to the secondary lumen and has a slit longitudinally along its length. The slit permits radial expansion to accommodate tools having a radius larger than that of the secondary lumen, which preferably is made of a flexible material that expands. A connector is attached to the proximal end of the primary lumen and connects to the body of the endoscope. The connector extends longitudinally to accommodate different length insertion tubes. Optionally, an adapter can be used to attach the connector to the body of the endoscope. Varying the adapter permits the sheath device to be attached to various endoscope bodies.

16 Claims, 11 Drawing Sheets

(56) References Cited

U.S. PATENT DOCUMENTS

| | | |
|---|---|---|
| 6,530,881 B1 | 3/2003 | Ailinger et al. |
| 6,793,661 B2 | 9/2004 | Hamilton et al. |
| 6,863,651 B2 | 3/2005 | Remijan et al. |
| 6,911,005 B2 | 6/2005 | Ouchi et al. |
| 7,081,097 B2 | 7/2006 | Martone et al. |
| 8,845,518 B2 | 9/2014 | Oneda et al. |
| 2003/0114732 A1 | 6/2003 | Webler et al. |
| 2003/0130564 A1* | 7/2003 | Martone ............ A61B 1/00071 600/121 |
| 2007/0270646 A1 | 11/2007 | Weiner |
| 2012/0316391 A1 | 12/2012 | Weitzner et al. |

\* cited by examiner

DISPOSABLE SHEATH DEVICE

FIELD OF THE INVENTION

The invention relates to endoscopy, including cystoscopy, and more particularly to a disposable device for protecting an endoscope or cystoscope from a non-sterile environment so that the endoscope or cystoscope can be used again without the necessity for sterilization.

BACKGROUND OF THE INVENTION

Endoscopes are useful for diagnostic and therapeutic indications. They have been optimized to improve performance for particular purposes. Thus, there are endoscopes for examination of esophagus, stomach, duodenum and the like. Colonoscopes are specialized for examining the colon. Cystoscopes are specialized for examining the bladder, urethra and kidneys. Angioscopes are specialized for examining blood vessels. Bronchoscopes are specialized for examining the bronchi. Laproscopes are specialized for examining the peritoneal cavity. Arthroscopes are specialized for examining joint spaces. All of these devices are endoscopes. The devices generally are expensive and used in a contaminated environment. Thus, they are not one use devices and must be sterilized between uses so as not to spread contamination such as, for example, infection or disease.

It has been known to use sheath devices providing detachable covers for the viewing tube of the endoscope that is inserted into a body cavity. U.S. Pat. No. 6,911,005 describes a detachable sheath having an inner diameter smaller than the outer diameter of the viewing tube for an endoscope having an air feeding tube that is used to feed air into the sheath for inserting the viewing tube into the sheath. It also describes sheaths having an inner diameter larger than the outer diameter of the viewing tube. The viewing tube is inserted into the sheath device which is stretched over the viewing tube to reduce the diameter of the sheath device.

U.S. Pat. No. 4,646,722 discloses creating a variety of specialized endoscopes by using protective sheaths having various special purpose medical instruments mounted at the end of a biopsy channel and operated through the channel. U.S. Pat. No. 7,081,097 discloses a sheath assembly adapted for use with an endoscopic viewing tube where the sheath has a biopsy sampling device attached to the sheath including a collection member proximate the end.

U.S. Pat. No. 4,991,565 discloses providing an endoscope with a sheath that is removably fitted over the viewing tube and appears to have a plurality of channels for passing fluids provided within the sheath, each channel having an opening on at one end near the distal end portion of the sheath and extending at the other end past the proximal end of the sheath.

U.S. Pat. No. 6,793,661 discloses an endoscopic sheath having an inflatable member coupled to and surrounding a portion of the sheath body and adapted to be inflated radially. The sheath assembly further includes an expansion-inhibiting mechanism coupled to at least one of the inflatable member and the sheath body portion. The expansion-inhibiting mechanism inhibits longitudinal expansion of the sheath body portion during inflation of the inflatable member. Optionally, the sheath assembly may include a channel that extends longitudinally along the outer surface of the sheath body portion.

U.S. Pat. No. 8,845,518 discloses apparatus and methods for attaching and forming enclosed inflatable members on an endoscope assembly with a disposable sheath. A flexible and resilient cuff is fixed on the outer surface of the disposable sheath to form an annular space for inflation through a lumen internal to the sheath.

U.S. 2003/0114732 discloses a sheath for use with intra-corporeal optical imaging instruments such as imaging guidewires, catheters or endoscopes. Also disclosed are sheath devices having multiple lumens longitudinally attached to each other at an exterior portion of the lumens.

U.S. 2007/0270646 discloses a disposable sheath for use with a cystoscope or endoscope. In one aspect of the disclosure the sheath includes an exterior wall and has a first channel and a second channel within the exterior wall of the sheath.

Although disposable sheaths have been known and used for some time, it appears that they have been designed and adapted for specific endoscopes by respective endoscope manufacturers. Indeed each type of endoscope may have slightly different measurements. It would be desirable to have a disposable sheath system that is adapted to be used on more than one manufacturer's endoscope for the particular type of endoscope such as, for example, a ureteroscope. Such a disposable sheath can be more economical and avoid the necessity for suppliers to store various disposable sheaths to fit the various endoscopes made by different manufacturers.

SUMMARY OF THE INVENTION

The present invention provides a disposable sheath system for an endoscope having an insertion (viewing) tube. The disposable sheath system comprises a primary lumen, at least one secondary lumen attached to the exterior of the primary lumen, a connector for attaching the lumens to the body of the endoscope, the connector being adapted to expand longitudinally in the direction of the length of the primary lumen to accommodate a range of lengths for the viewing tubes, and at least one secondary lumen having therein a split insert commensurate in length with the secondary lumen for inserting a tool device therethrough. Optionally, the disposable sheath system also comprises an adapter piece that attaches the connector to the body of the endoscope for endoscopes having a different structure than that for which the connector is adapted to fit.

The present disposable sheath system is particularly useful in connection with a rigid cystoscope having an insertion (viewing) tube, which may have different length tubes depending upon the manufacturer. The secondary lumen is provided to insert a tool to be used in combination with the viewing tube. The split insert in the secondary lumen permits the use of a tool having a diameter slightly larger than the interior diameter of the tube defining the secondary lumen.

Potential advantages of the use of a disposable sheath system in accord with the present invention instead of a currently common (conventional) rigid cystoscopy lens include less equipment to resterilize and, thus, less chance of contamination (and avoiding risk of improper sterilization, etc.). Also, the existing process of sterilizing conventional scopes between office procedures can lead to delay in appointments. In addition, conventional process of sterilizing scopes can be an issue when the sterizilizer is broken, the sterilization process is subject to regulatory change(s) (e.g., CIDEX is no longer utilized), or when the steriziling process results in scope damage (which occurs most often in the instance of flexible scopes, when the seal/coating is broken with repeated sterilizing).

The disposable sheath of the present invention can be used with existing office equipment (no need for new lens, irrigation supplies, etc.). It provides a potentially smaller outer diameter for the sheathed scope for insertion with a closed working channel (e.g., for routine surveillance cystoscopy), and may be less traumatic/more comfortable for the patient. The softer sheath material (as compared to the conventional metallic sheath) also may be less traumatic/more comfortable for the patient. The conventional metal sheath typically encloses both the viewing tube and a tool channel. The collapsable second (tool) lumen of the present invention is exterior to the primary lumen that encloses the viewing tube. Thus, the OD (outer diameter) of the sheath system of the present invention can be smaller for insertion into the patient.

If the disposable sheath is indeed more comfortable for office cystoscopy using a conventional rigid scope, it may be a competitive alternative to flexible cystoscopy because the rigid scope lens features increased light and better optics (presently, it is understood that many urologists use flexible cystoscopy for men in the office, because it is easier and more comfortable than conventional rigid cystoscopy—this disposable sheath device may avoid that discomfort).

Flexible scopes are expensive to purchase and expensive to repair. Using a sheath in accord with the present invention may reduce repairs due to no need for sterilization, hence making this sheathed scope option more appealing.

The disposable scope sheath in accord with the present invention has a much larger working channel (second lumen) than the conventional flexible cystoscope, making it more useful in the office for office procedures. With the flexible disposable sheath design, it is much easier to use this as a catheter/drain initially to empty the bladder prior to cystoscopy. Also, the flexible sheath can potentially be used for serial urethral dilation (i.e., for urethral dilation) with insertion of stiffeners with progressively larger diameters.

Disposable sheath systems in accord with the present invention can be cheaper and more efficient to use because there would be a faster turnaround for a doctor treating multiple patients in the office. No re-sterilization is required after use. No need to use or sterilize the stainless steel equipment holding the conventional rigid scope and far less equipment required to maintain patient care. Only one scope would be needed for the doctor to treat multiple patients because a new sheath can be used for each patient. There would be no need to use one and, then, take a second one out for the next patient while the first one is being sterilized.

Additionally, with multiple external secondary lumens, for example, a guide wire could be placed through one secondary external lumen while irrigation is achieved through another secondary external lumen, and a laser fiber (or stone basket) can be used through a further secondary external lumen. This could save quite a few steps in the procedure. The expandability of the external secondary lumen potentially is useful also to extract a stone/fragment through the lumen with a basket, again saving the step of withdrawing and reinserting the scope. Yet, insertion of the scope protected by the primary lumen is relatively easy because of the smaller diameter with the secondary exterior lumens collapsed.

Other advantages of the present disposable sheath system will become apparent upon consideration of the detailed description and drawings. Although the disclosure uses a ureteroscope as an example, many of the benefits of the disposable sheath system can also be achieved when using flexible scopes.

DETAILED DESCRIPTION

In accord with the present invention, a disposable sheath system for an endoscope having a viewing tube, the disposable sheath system comprises a primary lumen, at least one secondary lumen attached along the length of the exterior of the primary lumen, and a connector for attaching the lumens to the body of the endoscope. The connector is adapted and arranged to expand longitudinally in the direction of the length of the primary lumen to accommodate a range of lengths for the viewing tubes. At least one secondary lumen includes therein a split insert commensurate in length with the secondary lumen for inserting a tool device therethrough. In one embodiment, the disposable sheath system also comprises an adapter piece that attaches the connector to the body of the endoscope for endoscopes having a different structure than that for which the connector is adapted to fit.

One embodiment of the present disposable sheath system will be described, for example, in more detail in connection with a ureteroscope having a viewing tube. Different manufacturers may make the ureteroscope with somewhat different length viewing tubes. Indeed each type of endoscope may have slightly different measurements. Although each type of endoscope generally will require a particular disposable sheath system, disposable sheath systems in accord with the present invention can be used to accommodate some range of differences, for example, in length of viewing tubes in the specific types of endoscopes.

Figure 1A:
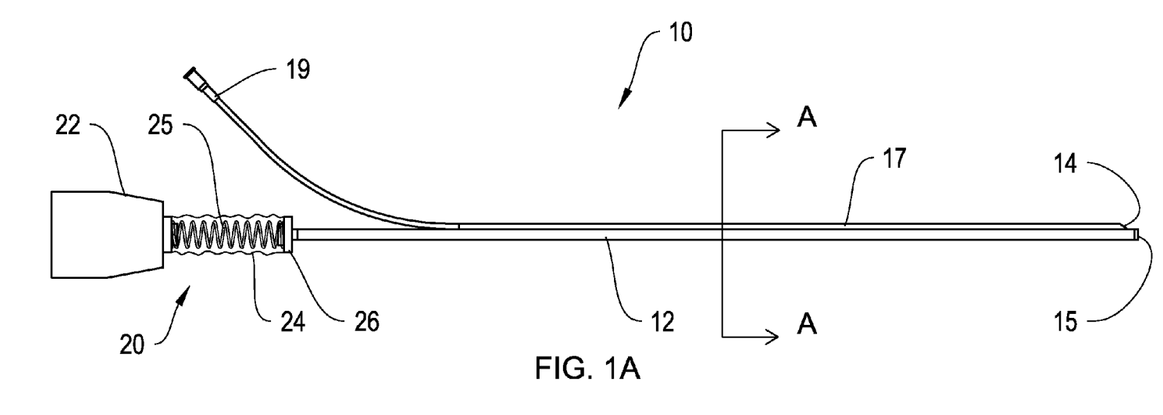
FIG. 1A is a side elevational view of one embodiment of a disposable sheath system in accord with the present invention.
Figure 1B:
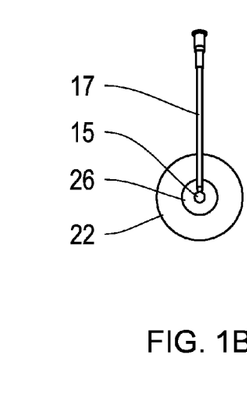
FIG. 1B is an end view of the disposable sheath system of FIG. 1A from the distal end of the device.

With respect to a disposable sheath system for a ureteroscope in accord with the present invention, FIGS. 1A, 1B, 1C and 2 illustrate one embodiment. The disposable sheath device 10, as illustrated in FIG. 1A, has a primary lumen 12 having a viewing window 15 at its distal end. Attached along a length on the exterior of the primary lumen 12 is a secondary lumen, generally of smaller diameter than the primary lumen. The secondary lumen has an opening at the distal end 18 and an opening provided by a fitting 19 at the proximal end. The fitting 19 at the proximal end of the secondary lumen is provided to facilitate insertion of a tool device, as needed, into the secondary lumen.

At the proximal end of the primary lumen 12 is a connector 20 that is attached to the primary lumen for attaching the disposable sheath system, for example, to a ureteroscope. The connector 20 has central opening, a body section 22 adapted and arranged to attach to a ureteroscope and a longitudinally expandable section for connecting to the primary lumen 12. The longitudinally expandable section 24 has a spring connected to the body section 22 at one end and to an end piece at the other end which attaches to the primary lumen. The spring 25 is enclosed by a flexible covering 24 that permits the spring 25 to extend longitudinally for accommodating various length viewing tubes.

Figure 1C:
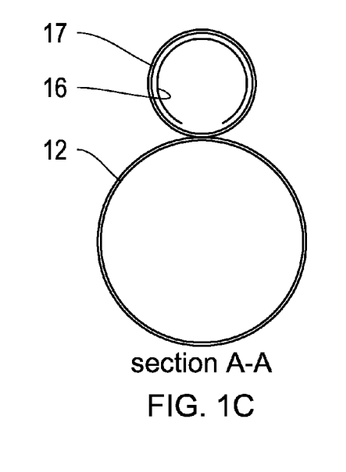
FIG. 1C is a cross-sectional view of the disposable sheath system of FIG. 1A taken at section A-A.
Figure 2:
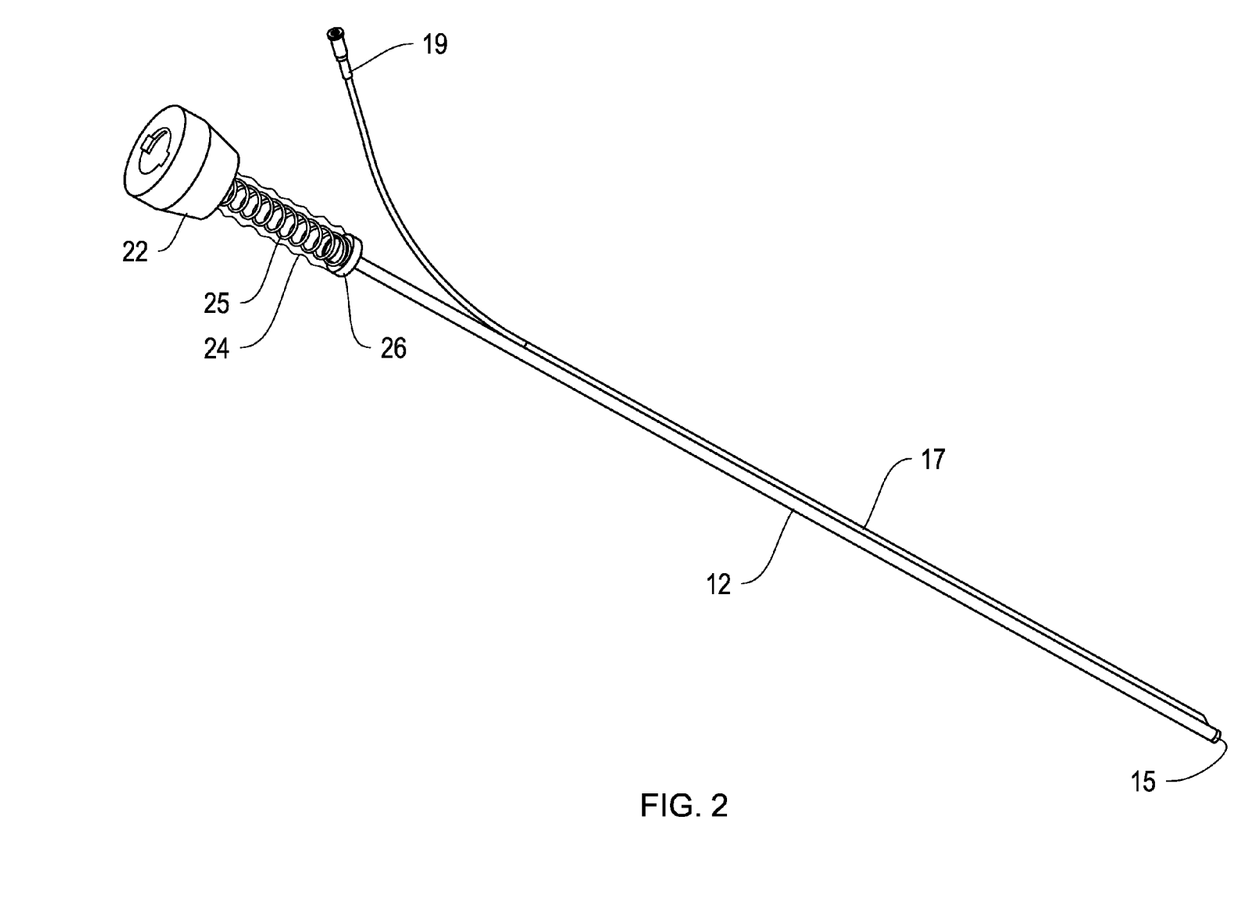
FIG. 2 is an isometric view of the disposable sheath system of FIG. 1A.

FIG. 1C illustrates the primary lumen 12 attached to the secondary lumen 17. The secondary lumen has an insert that is split along its length (note gap in circumference of the split insert) so as not to completely encircle a device inserted therein.

Figure 3A:
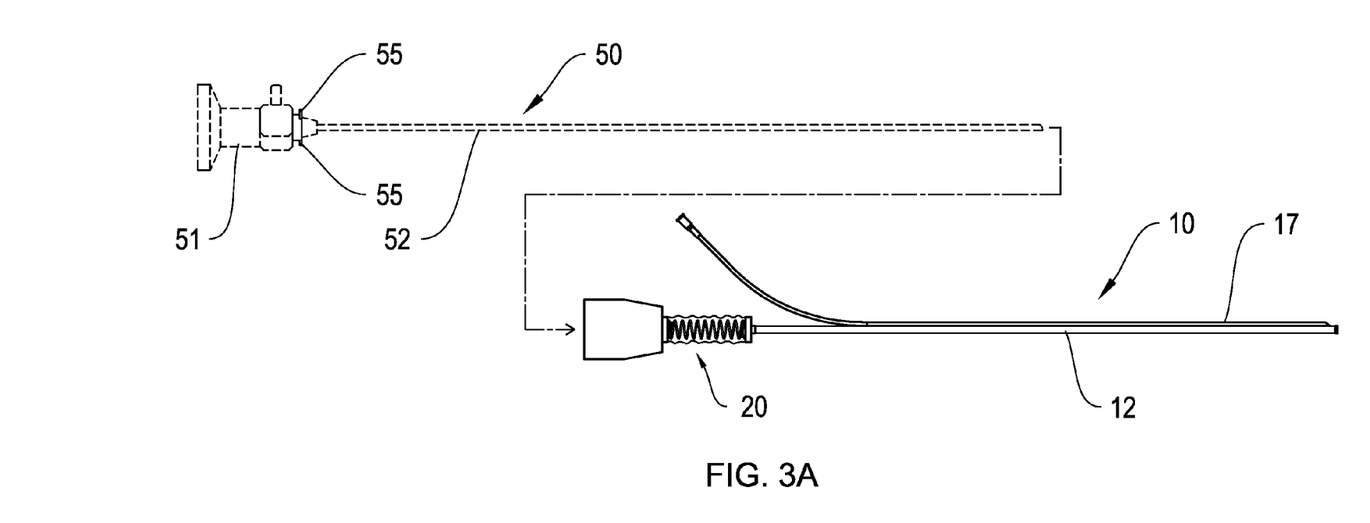
FIGS. 3A-3D illustrate the insertion of an ureteroscope into the disposable sheath system of FIG. 1A to provide a sheathed ureteroscope.
Figure 3B:
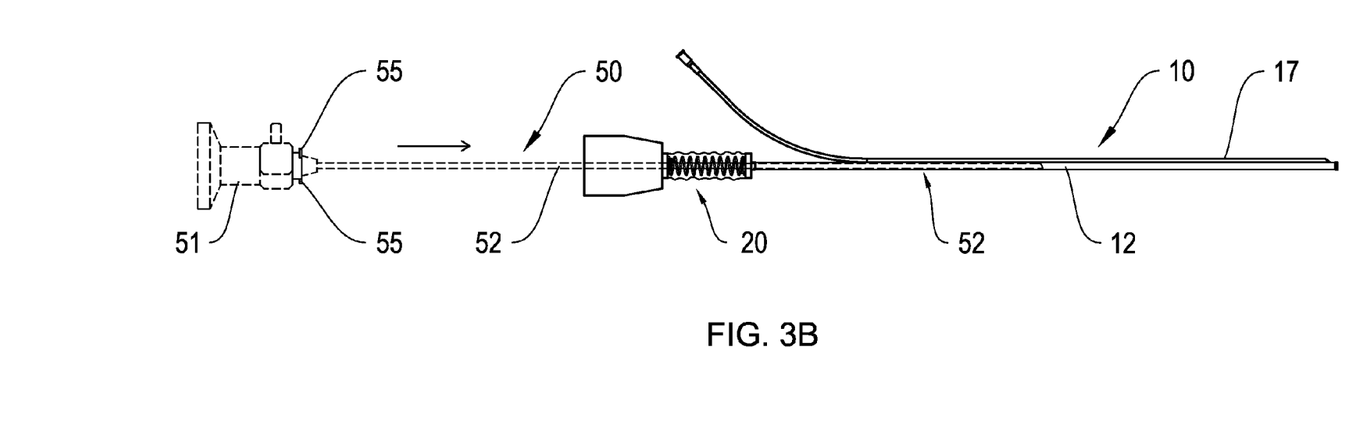
Figure 3C:
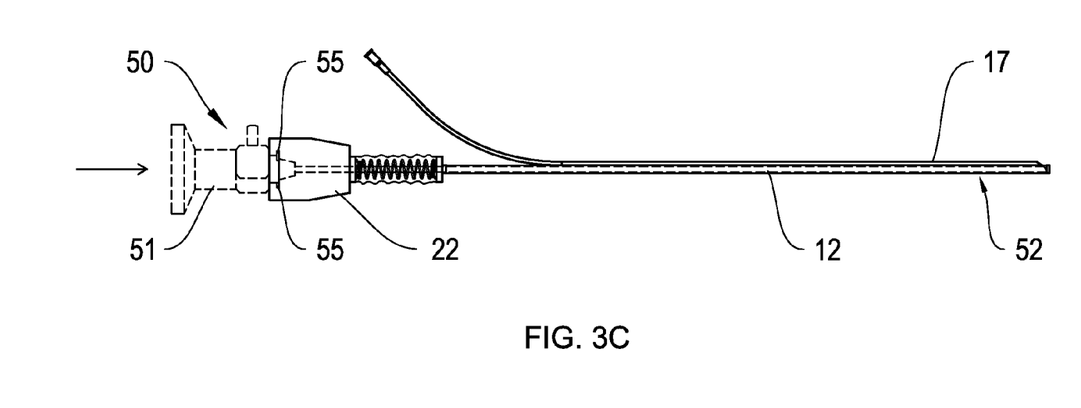
Figure 3D:
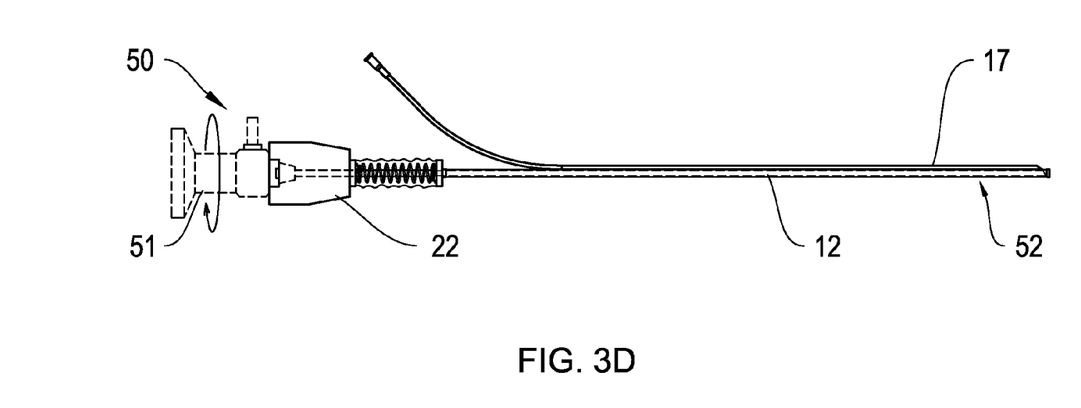

As illustrated in FIGS. 3A-3D, a ureteroscope 50 having a body 51 and a viewing tube 52 is inserted into the disposable sheath system 10. The viewing tube 52 is inserted into the disposable heath system 10 by first inserting the viewing tube into the connector 20 at the proximal end of the disposable sheath system (FIG. 3A). Insertion continues until the distal end of the viewing tube abuts the viewing window 15 of the primary lumen 12 (FIGS. 3B-3C). When the distal end of the viewing tube abuts the viewing window 15 of the primary lumen 12, the body 51 of the ureteroscope is partially within the connector body section 22 of the sheath system (see FIG. 3C). Two pins 55 extending radially 180 degrees apart on the body of the ureteroscope engage openings in the body section 22 of the sheath system. A 90 degree rotation of the ureteroscope body 51 with respect to the connector body section 22 (FIG. 3D) locks the ureteroscope and sheath system together through the pins 55.

Figure 4:
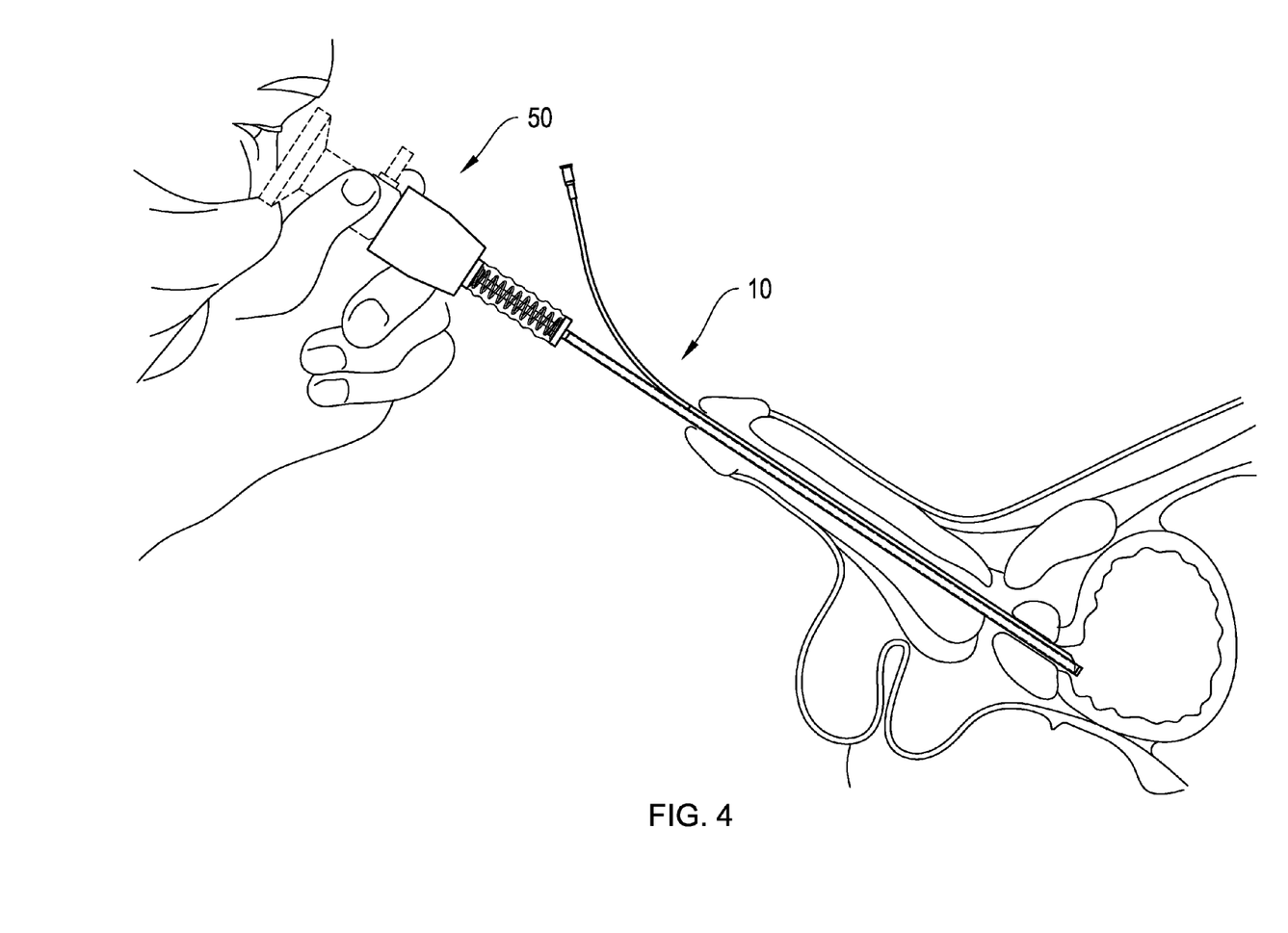
FIG. 4 is an isometric illustration of the sheathed ureteroscope of FIG. 3 inserted into male anatomy.

As illustrated in FIG. 4, with respect to male anatomy, a healthcare professional can easily use the ureteroscope by conventional manipulation.

Figure 5A:
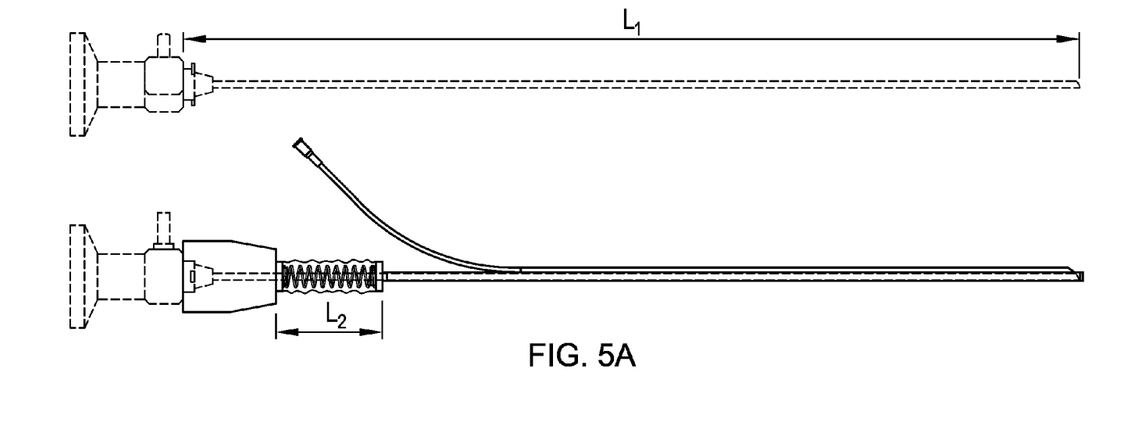
FIGS. 5A-5B illustrate how the disposable sheath system of FIG. 1A accommodates an ureteroscope having a viewing tube of length L1 as well as another ureteroscope having a longer viewing tube of length L3.
Figure 5B:
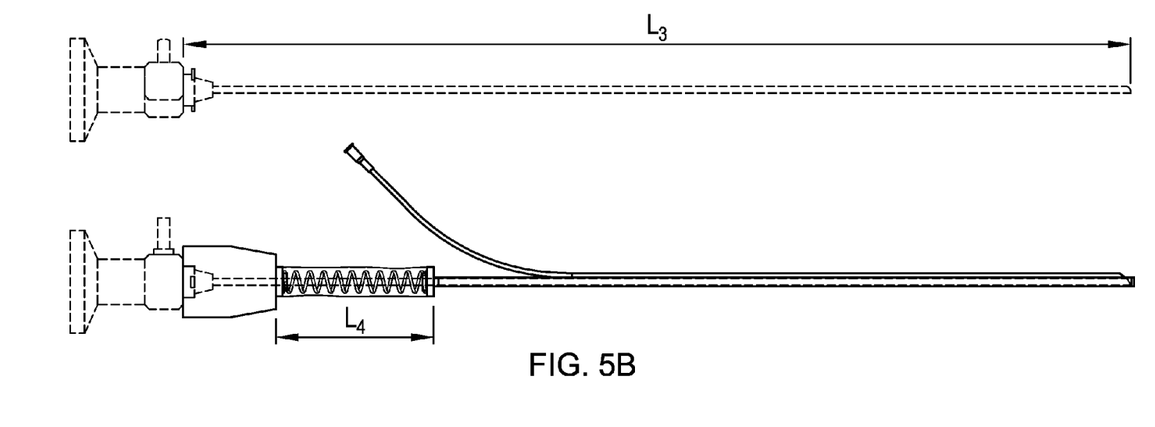

The longitudinally expandable section of the connector 20 conveniently allows for accommodating ureteroscopes of various lengths made by different manufacturers. As illustrated in FIG. 5A, a first ureteroscope having a viewing tube of length $L_1$ can be inserted into a disposable sheath system in accord with the present invention with the spring of the connector having a length $L_2$. When a ureteroscope having a longer viewing tube $L_3$ is inserted into the sheath system in accord with the present invention, the spring and flexible cover of the connector expands to a spring length of $L_4$ to accommodate the longer viewing tube (FIG. 5B).

Figure 6A:
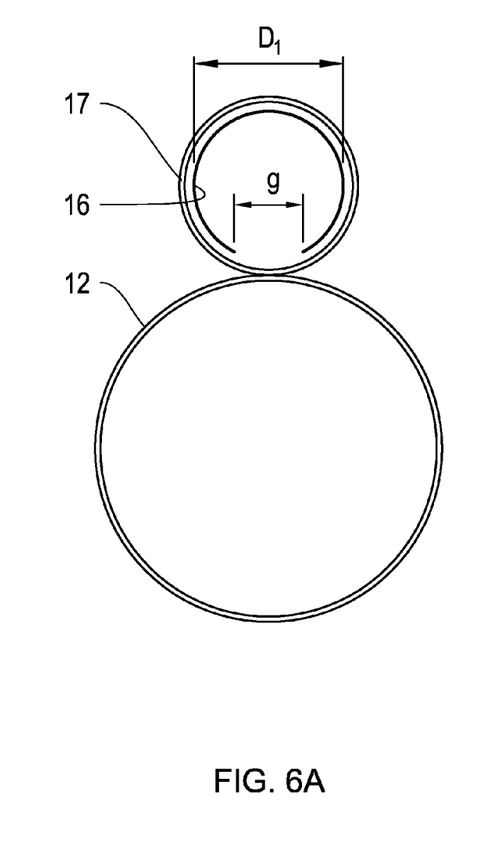
FIGS. 6A-6B illustrate how the split insert within the secondary lumen permits expansion of the diameter to permit use of a tool device having a diameter $D_2$ slightly larger than the interior diameter $D_1$ of the secondary lumen (note: gap g expands to gap g' for accommodation of larger diameter tool).
Figure 6B:
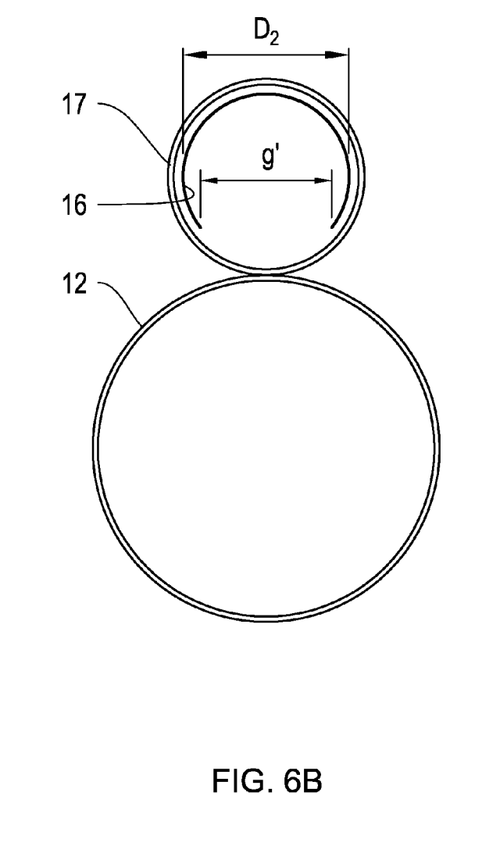

The secondary lumen 17 is provided for the use of various tools as needed by the healthcare provider. To accommodate for tools having various exterior diameters, the secondary lumen 17 is made of a sheath material having flexibility. Further, a split insert 16 is provided (FIG. 6A) inside the secondary lumen sheath. The split insert 16 has a gap g in the circumference for accommodating a tool having a diameter $D_1$ that is equal to the interior diameter of the sheath. However, a tool having a diameter $D_2$ that is slightly larger than the interior diameter of the sheath can be accommodated by a radial stretching of the sheath material and an enlarging of the gap g' of the split insert 16 in the secondary lumen (FIG. 6B).

Figure 7A:
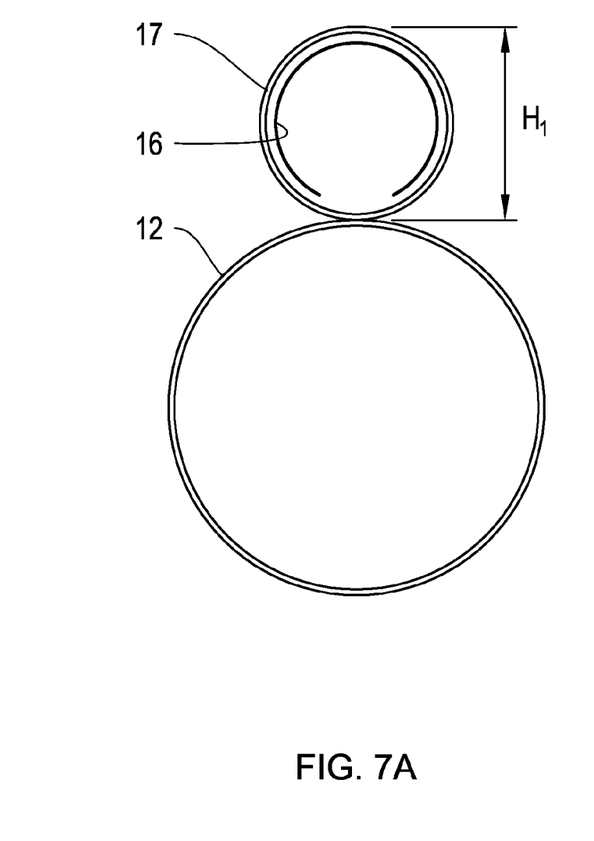
FIGS. 7A-7B illustrate how the secondary lumen is collapsible for insertion of a sheathed ureteroscope into a patient.
Figure 7B:
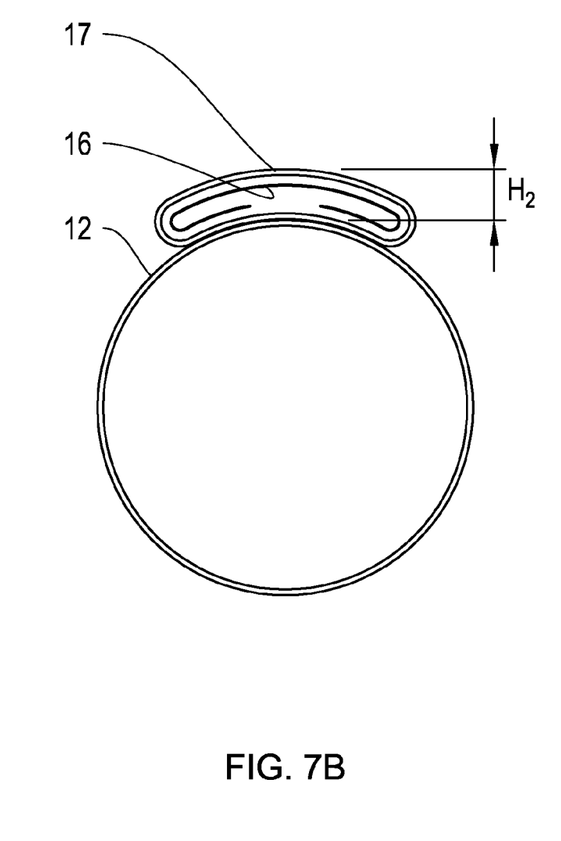

As illustrated in FIGS. 7A-7B, the secondary lumen having a height $H_1$ (i.e., the exterior diameter of the sheath) is adapted and arranged to collapse, having a height only of $H_2$, for insertion of the sheath system with ureteroscope into a patient. This is easier to insert (and more comfortable to the patient) than a conventional ureteroscope having a metal sheath that encloses both the viewing tube and a tool lumen, thus having a significantly larger diameter. The secondary lumen expands from collapsed position to full height when a tool device is inserted into the lumen as needed.

Figure 8:
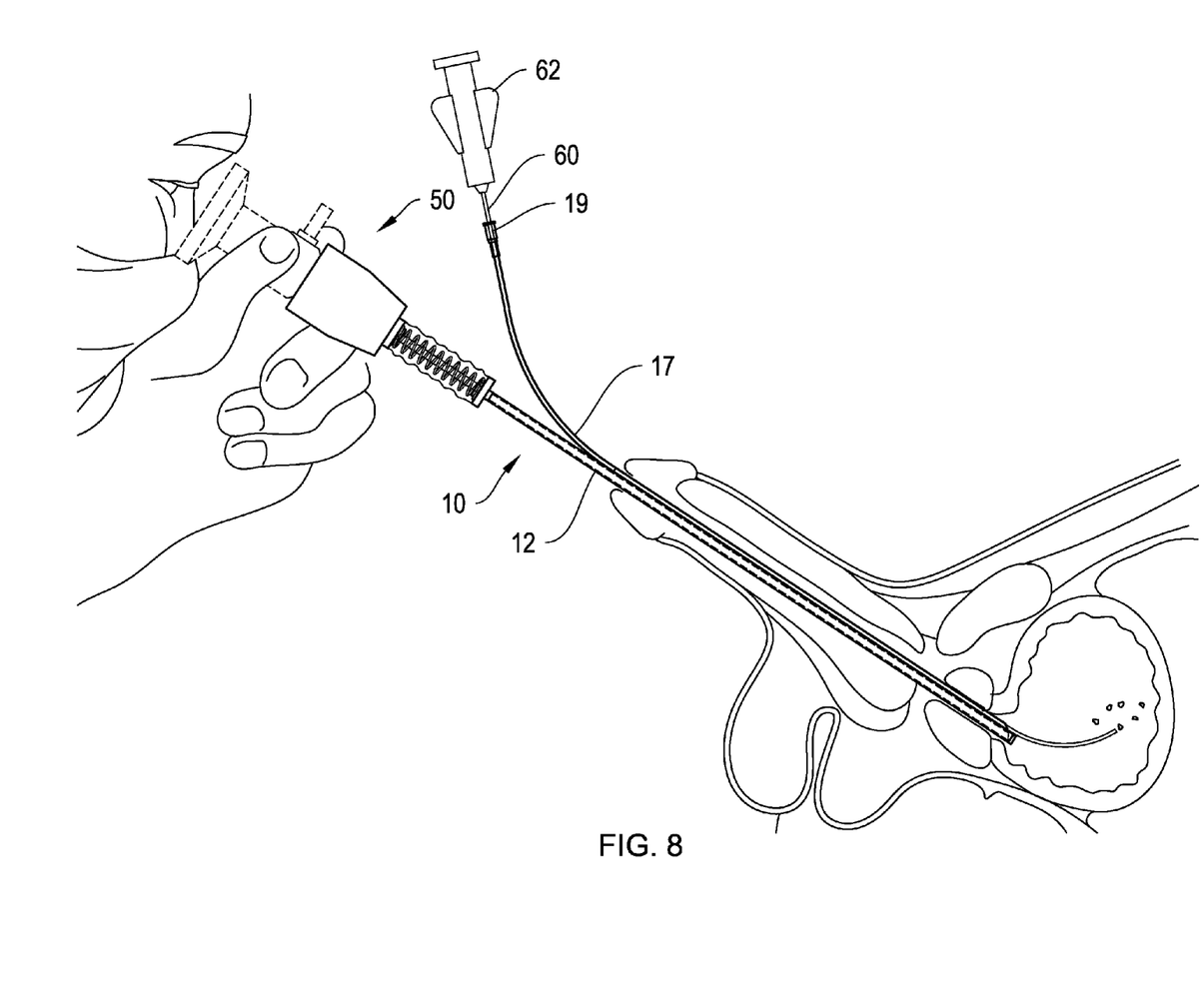
FIG. 8 is an isometric illustration of the sheathed ureteroscope of FIG. 3 in male anatomy further illustrating an irrigation device inserted into the secondary lumen and irrigating the bladder.
Figures 9A, 9B:
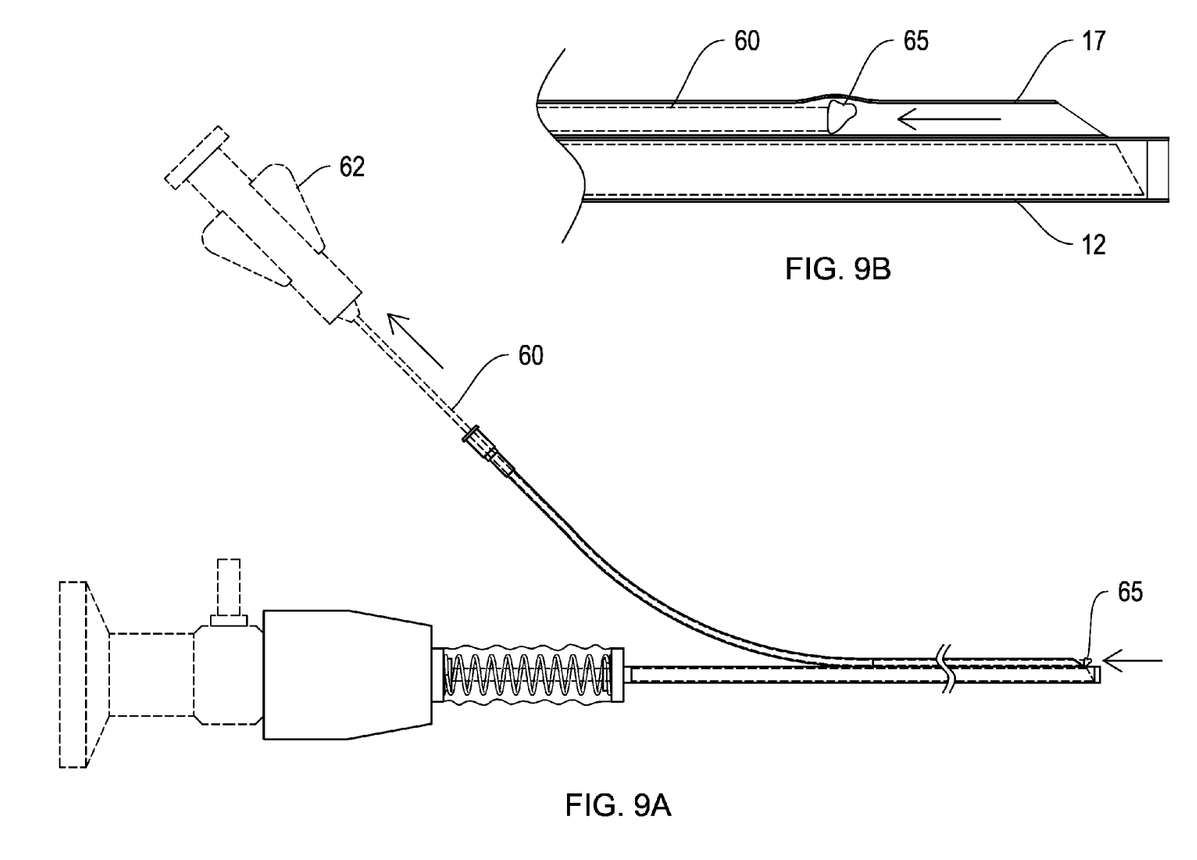
FIG. 9A is an illustration of removing an irrigation device through the secondary lumen where the distal end of the irrigation device has a larger diameter than the interior diameter of the secondary lumen.
FIG. 9B is an illustration showing how the split insert in the secondary lumen expands to permit the distal end of the irrigation device to be withdrawn through the secondary lumen.

One type of tool device that may be used while the ureteroscope is inserted into a patient is an irrigator device. As shown in FIG. 8, the irrigator device comprises a tube 60 connected to a syringe device 62 that is inserted into the secondary lumen as needed. When inserted, the irrigator may be used to irrigate a portion of tissue, or the like. The distal end 65 of the irrigator device may have a diameter that is larger than the interior diameter of the sheath of the secondary lumen 17 (FIG. 9A). The split insert 16 and flexible material of the sheath of the secondary lumen 17 accommodate the larger diameter of the distal end 65 of the irrigator device as illustrated in FIG. 9B.

Figure 10:
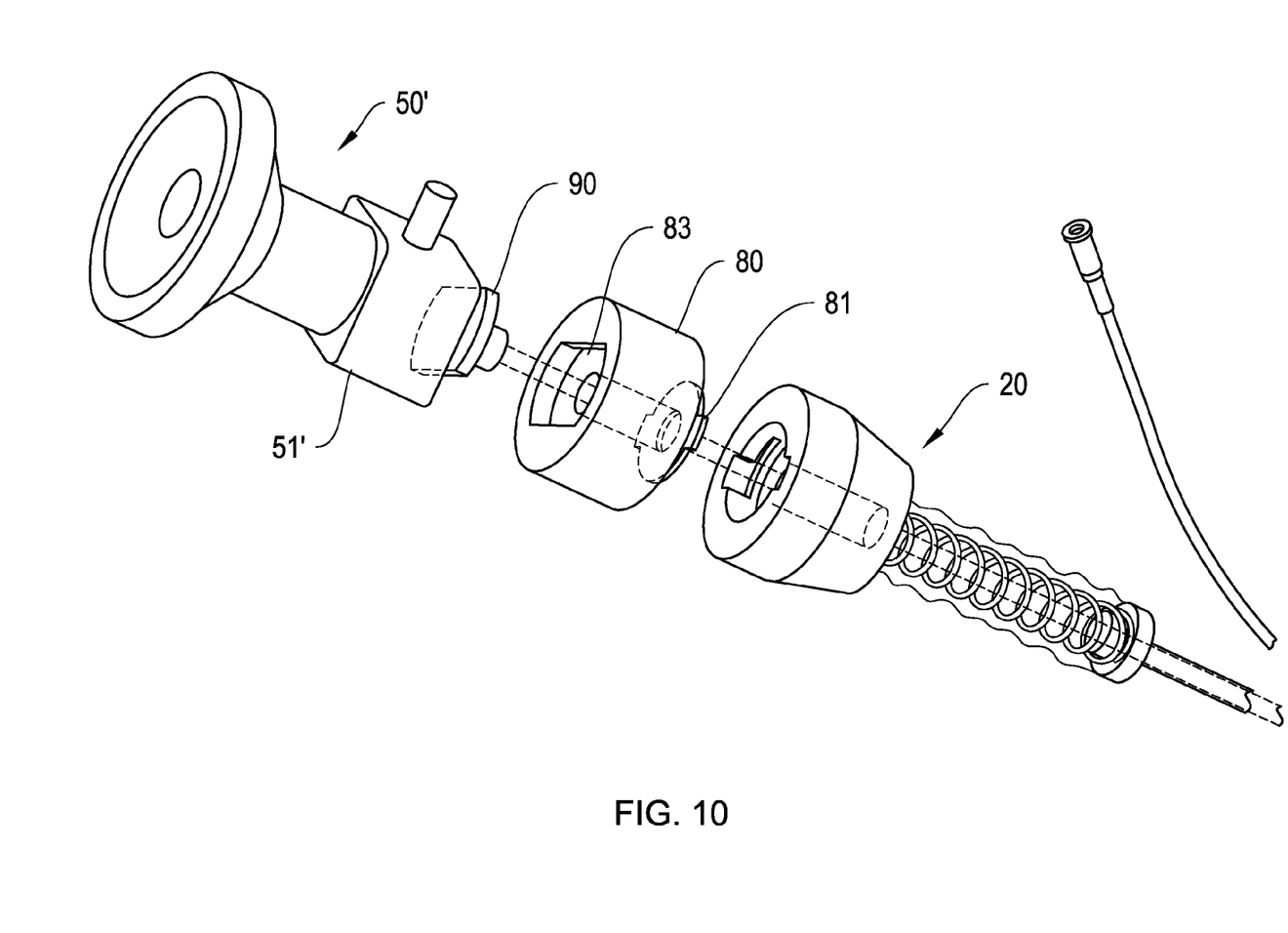
FIG. 10 is a partial isometric view of the proximal end of the disposable sheath system of FIG. 1A illustrating the use of an adapter to attach to the body of an ureteroscope.

As noted, different manufacturers may make ureteroscopes having somewhat different length viewing tubes. Also, the body of the ureteroscope may have a different configuration to which the connector of the disposable sheath system must be attached. In order to provide for various attachment configurations of different manufacturers, an adapter can be included in the sheath system. Then, the connector of the sheath system is adapted and arranged to attach to one of the configurations. An adapter is provided with the sheath system that is configured to attach at one end to the connector body section and at the other end adapted and arranged to attach to the body of the ureteroscope. For example, in FIG. 10, an adapter 80 is illustrated. The body 51' of the ureteroscope 50' has a configuration comprising a planar section 90 spaced slightly from the main body section. The connector 20 of the sheath system is configured to attach to two diametrically opposed radially extending surfaces 81, as illustrated. Therefore, the adapter must be configured at the end for attaching to the ureteroscope by having an opening to receive the planar section 90. The adapter 80 permits insertion of the planar section 90 and rotating the adapter 90 degrees to lock the ureteroscope body to the adapter. At the opposite end of the adapter, the connector is locked on.

The primary lumen 12 encloses the viewing tube of the scope. The material for this lumen must be flexible. In view of the expandable connector piece 20, it is not required to stretch longitudinally but preferably has some resilience to expand radially. Preferably, the primary lumen sheath material will have the properties of medium durometer, low elongation, high tear resistance and durability. Any medical device material having these properties can be used. Polyurethane film materials generally have desired properties for use in the present invention, however, but silicone films, latex or any flexible film-like material approved for medical use in a patient can be used. Controlling the wall thickness provides the desired features and the desired wall thickness can be readily determined by routine experimentation by those skilled in the art. Depending on the material used and the type of endoscope, wall thicknesses of the primary lumen sheath material can vary and can readily be determined by a person skilled in the art. Generally, for an ureteroscope as illustrated, the wall thickness is preferably from about 0.006 inch to about 0.009 inch.

The secondary lumen 17 provides access into the patient for tool devices as necessary. Materials suitable for the primary lumen sheath are also suitable for the secondary lumen sheath. However, it is highly desirable for the secondary lumen sheath material to be flexible and to stretch to expand radially to accommodate tools having an exterior diameter slightly larger than the interior diameter of the secondary lumen. Thus, the wall thickness of the secondary lumen sheath most likely will differ from that of the primary lumen. Again, polyurethane film materials generally have desired properties for use in the present invention, however, but silicone films, latex or any flexible film-like material approved for medical use in a patient can be used. Controlling the wall thickness to expand the lumen's diameter with minimal resistance when passing a tool device therethrough and to provide the desired features can be readily determined by routine experimentation by those skilled in the art. The more it is desired to permit the lumen to expand, the higher the resistance encountered by a particular material. Depending on the material used and the type of endoscope, wall thicknesses of the primary lumen sheath material can vary, for the various size tools that may be desired to be accommodated, and can readily be determined by a person skilled in the art. Generally, for an ureteroscope as illustrated, the wall thickness is preferably from about 0.003 inch to about 0.006 inch, most preferably 0.005 inch.

However, the resistance is of the secondary lumen sheath material can be reduced by using a low coefficient of friction material for the insert 16 that is positioned inside the secondary lumen and is between the tool device and the wall of the secondary lumen. The insert 16 generally will be made of a durable material having a high durometer, low elongation and high tear resistance. Because polyurethane, silicone, latex, and like materials typically have a relatively high coefficient of friction (i.e., a drag property), it is desirable to reduce the friction inside the secondary lumen for inserting or removing tools, biopsy segments, and the like through the small diameter secondary lumen. The longitudinal split of the insert 16 allows ready radial expansion inside the secondary lumen, particularly when the insert has a low coefficient of friction. A material, such as Mylar™ or the like, can provide high resistance to tear, high durometer and a relatively low coefficient of friction for the insert. Thus, the split insert 16 in the secondary lumen 17 allows tools slightly larger than the interior diameter of the secondary lumen to pass through the lumen contacting the low coefficient of friction insert and not contacting the higher coefficient of friction polyurethane, silicone, latex or the like. When in use, the insert opens the longitudinal split exposing only a small area of higher coefficient of friction material exposed by the gap (g, g') in the expanded insert. Other low coefficient of friction materials such as a thin film of polyethylene, or the like, can be used instead of Mylar™. Again, controlling the wall thickness to expand the lumen's diameter with minimal resistance when passing a tool device therethrough and to provide the desired features can be readily determined by routine experimentation by those skilled in the art. It has been found that use, for example, of a Mylar™ insert having a wall thickness of from about 0.00025 inch to about 0.00075 inch provides desirable results inside a polyurethane secondary lumen having a wall thickness of about 0.005 inch.

In many cases, lubricants are used to resolve such high coefficient of friction issues. Lubricants are surface treatments applied to the materials and generally work well, but have a tendency to migrate off the surface when inactive. Also, the lubricant can be removed relatively easily when encountering resistance of any kind such as when the lumen is expanded by a tool or solid material. The coating can be wiped off the surface exposing the high coefficient of friction the polyurethane, silicone, latex or the like materials. The use of an insert having a relatively lower coefficient of friction avoids issues typically accompanying use of a lubricant. When used, the lubricant of course must be medically compatible for the application. Suitable lubricants include, for example, 2% lidocaine jelly (sold under the mark "Urojet") and Surgilube™ which typically is used when patients are already under anesthesia.

Disposable sheath systems in accord with the present invention can be made by any suitable manufacturing process. One such process is described below. This is the manufacturing procedure allows one to adjust each sheath materials for the primary and secondary lumens independently to obtain the desired physical properties for that individual lumen. The sheaths when joined together create another physical property for the system that is the result of the differences in physical properties of the two sheaths joined lengthwise. With routine experimentation the resulting physical property attributes of the joined sheaths can be adjusted to create a system (joined tubes) that meets any physical requirement desired by the user. Sheath physical properties in each lumen that can be varied include durometer, elongation, wall thickness, materials and material features.

One useful manufacturing process involves the following steps:

Primary lumen sheath:
1. Cast a film of the desired polyurethane on a stainless steel rod. The rod will have the OD to result in the desired ID of the lumen and a length to provide a lumen for the particular type of endoscope.
2. Continue the cast films on the rod inverting each time until the proper wall thickness is achieved.

Secondary lumen sheath:
1. Cast a film of the desired polyurethane on a rod. The rod will have the OD to result in the desired ID of the lumen and a length equal to the length of rod used for making the primary lumen.
2. Continue the cast films on the rod inverting each time until the proper wall thickness is achieved.

Joining lumens:
1. Join the two rods with films together at each end so they are parallel and have no spaces anywhere along there length.
2. Cast a film of the desired polyurethane on the joined rods.
3. Invert the joined rods and cast a second film.
4. Remove the films on the rods by injecting a solution between the films and rods in both lumens.
5. Slide the rods out the inside of each lumen, clean to remove release residue and let dry.

6. Trim the ends of the joined tubes so the larger lumen is longer than the smaller lumen.
7. Attach the exposed end of the larger tube to a circular ring that holds a spring at the opposite end.
8. Attach the opposite end of the spring to the small end of the hub that will hold the Scope.
9. Secure a plastic or equivalent cover to the hub and the spring's circular rings and seal. The cover will be attached loosely allowing it to expand when the spring is stretched.

Placing Mylar™ insert into secondary lumen:
1. Cut a piece of Mylar™ film or equivalent to a length and width that when inserted in the small lumen of the device the width covers the lumens ID.
2. Fold and insert the Mylar™ film into the small lumen leaving a small portion of Mylar exposed outside each end the small lumen.
3. Insert a piece of tubing larger than the ID of the small lumen on the device into the small lumen's ID. The tubing will be sized to pass oversized tools into the small lumen with Mylar™.
4. The tube captures and secure the Mylar™ at the junction where the two tubes join.
5. When the small lumen is expanded as a result of insertion of an oversized tool the Mylar™ separates where the Mylar™ film meets allowing passage of the tool with minimal resistance.
6. Secure with adhesive the exposed free tube to the attached thin wall tube on the device where they meet. Trim Mylar™ as required.
7. Add a drop of polyurethane in a solvent at the distal end of the small lumen to secure the Mylar™ to the open end of the small lumen. Trim lumen at an angle and remove excess materials.

Finishing disposable sheath system:
1. Secure an appropriate size luer to the opposite end of the exposed free tube exiting the small lumen.
2. Insert and fix a clear viewing window to the open end of the large lumen of the device.
3. Add lubricant to internal surfaces.

Those skilled in the art can readily provide other suitable manufacturing processes.

The primary lumen typically will have a diameter to accommodate the viewing tube of the type of endoscope for which it is made. Depending on the use, endoscopes have different size (diameter) viewing scopes. For example, for the 12 Fr size of the ureteroscope, the primary lumen typically will have an ID that exceeds 0.157 inch and be less than 0.170 inch.

The secondary lumen typically will have a diameter to accommodate tools having a size from about 6 French to about $7^+$ French. For any particular secondary lumen, the expansion typically will accommodate tools of various French sizes depending on the use of the scope (e.g., for the illustrated ureteroscope, from about 6 French to about $7^+$ French, preferably about 6.5 French sizes).

The invention has been described in detail with specific references to a disposable sheath system for a ureteroscope. However, those skilled in the art will recognize that the disposable sheath system can be tailored for various types of endoscopes. Further, multiple secondary lumens can be attached to the primary lumen to accommodate the use of more than one tool device simultaneously.

Although the invention has been described in detail, it will be apparent that numerous modifications may be made by those skilled in the art without departing from the spirit and scope of the invention.

The invention claimed is:
1. A disposable sheath device to be used in conjunction with an endoscope comprised of a body having an insertion tube with optics at a distal end, the disposable sheath device comprising:
a primary lumen having a proximal end and a distal end for covering and protecting the insertion tube from bodily contamination;
a connector attached to the proximal end of the primary lumen, the connector being structured and arranged for connecting the disposable sheath device to the body of the endoscope, the connector being adapted to extend longitudinally between the disposable sheath device and the body of the endoscope to accommodate different length insertion tubes; and
a second lumen having a radius to accommodate a desired tool and being attached exteriorly to a length of the primary lumen, the second lumen having an insert comprising a tubular body with a longitudinal slit formed therein extending a length of the insert, wherein the slit extends parallel to a longitudinal axis of the secondary lumen to permit radial expansion to accommodate devices having a radius larger than the radius of the second lumen, the tubular body of the insert being substantially commensurate in length to a length of the second lumen,
wherein the connector comprises a spring for longitudinal expansion to accommodate an endoscope having an insertion tube that is longer than can be accommodated when the spring is compressed.

2. The disposable sheath device of claim 1, wherein the primary lumen comprises a tube made of a flexible material suitable for medical use.

3. The disposable sheath device of claim 1, wherein the second lumen comprises a tube made of a flexible material suitable for medical use.

4. The disposable sheath device of claim 3, wherein the material is resilient to expand radially.

5. The disposable sheath device of claim 1, wherein the insert has a lower coefficient of friction than that of the second lumen.

6. The disposable sheath device of claim 1, wherein the primary lumen comprises a tube made of a flexible polyurethane material.

7. The disposable sheath device of claim 1, wherein the second lumen comprises a tube made of a flexible polyurethane material.

8. The disposable sheath device of claim 1, wherein the insert is made of a flexible Mylar™ material.

9. A disposable sheath device to be used in conjunction with an endoscope comprised of a body having an insertion tube with optics at a distal end, the disposable sheath device comprising:
a primary lumen having a proximal end and a distal end for covering and protecting the insertion tube from bodily contamination;
a second lumen having a radius to accommodate a desired tool and being attached exteriorly to a length of the primary lumen, the second lumen having an insert comprising a tubular body with a longitudinal slit formed therein extending a length of the insert, wherein the slit extends parallel to a longitudinal axis of the secondary lumen to permit radial expansion to accommodate devices having a radius larger than the radius of the second lumen, the tubular body of the insert being substantially commensurate in length to a length of the second lumen;

a connector attached to the proximal end of the primary lumen, the connector being structured and arranged for connecting the disposable sheath device to the body of the endoscope, the connector being adapted to extend longitudinally between the disposable sheath device and the body of the endoscope to accommodate different length insertion tubes; and an adapter for attaching to the connector, and being structured and arranged for connecting the disposable sheath device to the body of the endoscope, wherein the connector comprises a spring for longitudinal expansion to accommodate an endoscope having an insertion tube that is longer than can be accommodated when the spring is compressed.

10. The disposable sheath device of claim 9, wherein the primary lumen comprises a tube made of a flexible material suitable for medical use.

11. The disposable sheath device of claim 9, wherein the second lumen comprises a tube made of a flexible material suitable for medical use.

12. The disposable sheath device of claim 11, wherein the material is resilient to expand radially.

13. The disposable sheath device of claim 9, wherein the insert has a lower coefficient of friction than that of the second lumen.

14. The disposable sheath device of claim 9, wherein the primary lumen comprises a tube made of a flexible polyurethane material.

15. The disposable sheath device of claim 9, wherein the second lumen comprises a tube made of a flexible polyurethane material.

16. The disposable sheath device of claim 9, wherein the insert is made of a flexible Mylar™ material.

* * * * *